US008916536B2

(12) United States Patent
Schott

(10) Patent No.: US 8,916,536 B2
(45) Date of Patent: Dec. 23, 2014

(54) BONE-TARGETING BISPHOSPHONATE DUPLEX DRUGS

(76) Inventor: Herbert Schott, Tubingen (DE)

( * ) Notice: Subject to any disclaimer, the term of this patent is extended or adjusted under 35 U.S.C. 154(b) by 123 days.

(21) Appl. No.: 13/814,172

(22) PCT Filed: Aug. 3, 2011

(86) PCT No.: PCT/EP2011/063326
§ 371 (c)(1),
(2), (4) Date: May 13, 2013

(87) PCT Pub. No.: WO2012/016994
PCT Pub. Date: Feb. 9, 2012

(65) Prior Publication Data
US 2013/0237494 A1    Sep. 12, 2013

(30) Foreign Application Priority Data

Aug. 4, 2010    (EP) .................................. 10171886

(51) Int. Cl.
| | | |
|---|---|---|
| A01N 43/04 | (2006.01) | |
| A61K 31/70 | (2006.01) | |
| C07H 19/09 | (2006.01) | |
| C07F 9/6558 | (2006.01) | |
| C07H 19/073 | (2006.01) | |
| C07H 15/00 | (2006.01) | |
| A61K 45/06 | (2006.01) | |
| A61K 31/7068 | (2006.01) | |
| C07F 9/6512 | (2006.01) | |
| C07D 239/54 | (2006.01) | |

(52) U.S. Cl.
CPC ............ C07F 9/65127 (2013.01); C07H 19/09 (2013.01); C07F 9/65586 (2013.01); C07H 19/073 (2013.01); C07H 15/00 (2013.01); A61K 45/06 (2013.01); A61K 31/7068 (2013.01); C07D 239/54 (2013.01)
USPC ................. 514/49; 514/42; 514/43; 536/28.1; 536/28.4

(58) Field of Classification Search
None
See application file for complete search history.

(56) References Cited

U.S. PATENT DOCUMENTS

| | | | |
|---|---|---|---|
| 2006/0188542 A1 | 8/2006 | Bobyn et al. | |
| 2009/0227544 A1 | 9/2009 | Karpeisky et al. | |

FOREIGN PATENT DOCUMENTS

EP            0084822 A2    8/1983

OTHER PUBLICATIONS

Adzamli et al., "Phosphonate-Modified GdDTPA Complexes. II. Evaluation in a Rat Myocardial Infarct Model", *Investigative Radiology*, vol. 26, 143-148 (1991).

Adzamli et al., "Phosphonate-Modified Gd-DTPA Complexes. III: The Detection of Myocardial Infarction by MRI", *Magn Reson Med* 29, 505-511 (1993).
Bhushan et al., "Synthesis of Conjugatable Bisphosphonates for Molecular Imaging of Large Animals", *Angew. Chem. Int. Ed.*, 46, 7969-7971 (2007).
Brown et al., "Bone Turnover Markers as Predictors of Skeletal Complications in Prostate Cancer, Lung Cancer, and Other Solid Tumors", *Journal of National Cancer Institute*, vol. 97(1), 59-69 (2005).
Budman et al., "Zoledronic Acid (Zometa®) Enhances the Cytotoxic Effect of Gemcitabine and Fluvastatin: In vitro Isobologram Studies with Conventional and Nonconventional Cytotoxic Agents", *Oncology*, 70, 147-153 (2006).
Chen et al., "Synthesis of 3-1',1'-Ethylbisphosphonates-5-Fluorouracil and Preliminary Test for Its Bone Targeting Ability", *West China Journal of Pharmaceutical Sciences*, vol. 20 (1), 1 page (2005).
Choi et al., "The effects of topical application of bisphosphonates on replanted rat molars", *Dental Traumatology*, 26, 476-480 (2010).
Clezardin, "Anti-tumour activity of zoledronic acid", *Cancer Treatment Reviews*, 31, S1-S8 (2005).

(Continued)

*Primary Examiner* — Patrick Lewis
(74) *Attorney, Agent, or Firm* — Viksnins Harris & Padys PLLP

(57) ABSTRACT

The present invention relates to novel bisphosphonate duplex drugs, methods for preparing said compound; pharmaceutical compositions containing the same; as well as the use of said compounds in human and veterinary medicine, and, in particular, for treating tumors, viral infections; or dental disorders.

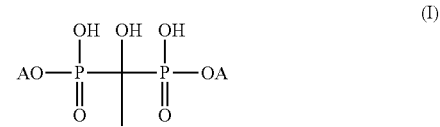

(I)

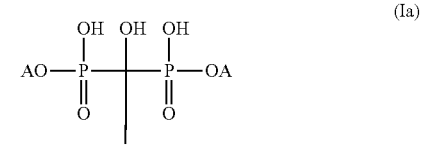

(Ia)

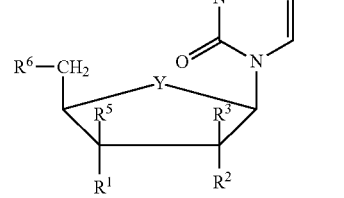

14 Claims, No Drawings

(56) References Cited

OTHER PUBLICATIONS

Coleman et al., "Risks and benefits of bisphosphonates", *British Journal of Cancer*, 98, 1736-1740 (2008).
Coleman et al., "New results from the use of bisphosphonates in cancer patients", *Current Opinion in Supportive and Palliative Care*, 3, 213-218 (2009).
Divakar et al., "4-(1,2,4-Triazol-1-yl)-and 4-(3-Nitro-1,2,4-triazol-1-yl)-1-(β-D-2,3,5-tri-O-acetylarabinofuranosyl)pyrimidin-2(1H)-ones. Valuable Intermediates in the Synthesis of Derivatives of 1-β-D-Arabinofuranosyl)cytosine (Ara-C)", *J. Chem. Soc., Perkin Trans.*, 1, 1171-1176 (1982).
Fabulet et al., "Synthesis of Gem-Bisphosphonic Doxorubicin Conjugates", *Phosphorus Sulfur and Silicon*, vol. 101, 225-234 (1995).
Fleisch, "Bisphosphonates, Pharmacology and Use in the Treatment of Tumour-Induced Hypercalcaemic and Metastatic Bone Disearse", *Drugs*, 42(6), 919-944 (1991).
Gao et al., "Synthesis of Uridine Derivatives Containing Amino Acid Residues", *Synthetic Communications: An International Journal for Paid Communication of Synthetic Organic Chemistry*, 33(15), 2635-2641 (2003).
Ghosh et al., "Effects of Bisphosphonates on the Growth of *Entamoeba histolytica* and *Plasmodium* Species in Vitro and in Vivo", *J. Med. Chem.*, 47, 175-187 (2004).
Kalek et al., "A direct method for the synthesis of nucleoside 5'-methylenebis(phosphonate)s from nucleosides", *Tetrahedron Letters*, 46, 2417-2421 (2005).
Kieczykowski et al., "Preparation of (4-Amino-1-Hydroxybutylidene) bisphosphonic Acid Sodium Salt, MK-217 (Alendronate Sodium). An Improved Procedure for the Preparation of 1-Hydroxy-1,1-bisphosphonic Acids", *J. Org. Chem.*, vol. 60(25), 8310-8312 (1995).
Knight et al., "Pilot studies of the effect of zoledronic acid (Zometa®) on tumor-derived cells ex vivo in the ATP-based tumor chemosensitivity assay", *Anti-Cancer Drugs*, vol. 16(9), 969-976 (2005).
Kubicek et al., "A Bisphosphonate Monoamide Analogue of DOTA: A Potential Agent for Bone Targeting", *J. Am. Chem. Soc.*, 127, 16477-16485 (2005).
Leu et al., "Relative binding affinities of bisphosphonates for human bone and relationship to antiresorptive efficacy", *Bone* 38, 628-636 (2006).
Migianu et al., "Novel Approach to Nucleoside-5'-(1-Hydroxymethylene-1, 1-Bisphosphonates): Synthesis of new AZT Analogues#" *Nucleosides, Nucleotides, and Nucleic Acids*, 24(2), 121-133 (2005).
Monkkonen et al., "Bisphosphonate-induced ATP analog formation and its effect on inhibition of cancer cell growth", *Anti-Cancer Drugs*, 19, 391-399 (2008).
Nancollas et al., "Novel insights into actions of bisphosphonates on bone: Differences in interactions with hydroxyapatite", *Bone* 38, 617-627 (2006).
Neville-Webbe et al., "Sequence- and Schedule-Dependent Enhancement of Zoledronic Acid Induced Apoptosis by Doxorubicin in Breast and Prostate Cancer Cells", *Int. J. Cancer*, 113, 364-371 (2005).
Pan et al., "Biodistribution and Pharmacokinetic Studies of Bone-Targeting N-(2-Hydroxypropyl)methacrylamide Copolymer—Alendronate Conjugates", *Molecular Pharmaceutics*, vol. 5(4), 548-558 (2008).
Papapoulos, "Bisphosphonate actions: Physical chemistry revisited", *Bone* 38, 613-616 (2006).
Patent Cooperation Treaty, International Searching Authority, Search Report and Written Opinion for PCT/EP2011/063326, 11 pages, Dec. 8, 2011.
Roelofs et al., "Molecular Mechanisms of Action of Bisphosphonates: Current Status", *Clin. Cancer Res.*, 12(20 Suppl), 6222s-6230s (2006).
Sanders et al., "3-D QSAR Investigations of the Inhibition of *Leishmania major* Farnesyl Pyrophosphate Synthase by Bisphosphonates", *J. Med. Chem.* 46, 5171-5183 (2003).
Santini et al., "The antineoplastic role of bisphosphonates: from basic research to clinical evidence", *Annals of Oncology*, 14, 1468-1476 (2003).
Schott, "Preparative Isolation of Purine Oligonucleotides from Partial Hydrolyzates of Depyrimidinated DNA", *Preparative Scale-Chromatography*, vol. 46, Grushka, E., Ed.: New York Basel, 269-308 (1989).
Schott, "Synthese von 4-Alkylcytosinnucleosiden und deren cytostatische Wirkung im L1210 Leukamiemodell der Maus", *Liebigs Ann. Chem.*, 465-470 (1994).
Schott, "Wirkstoff-Recycling aus Altmedikamenten", *Pharm. Ztg.*, 146, 24, 3 pages (2001).
Schott et al., "$N^4$-[Alkyl-(hydroxyphosphono)phosphonate]-cytidine—New drugs covalently linking antimetabolites (5-FdU, araU or AZT) with bone-targeting bisphosphonates (alendronate or pamidronate)", *Bioorganic & Medicinal Chemistry*, 19, 3520-3526 (2011).
Schott et al., "Cytotoxicity of the new antimetabolite-bisphosphonate (5-FdU-alendronate) in comparison to standard therapeutics on breast and ovarian cancer cell lines in the ATP tumor chemosensitivity assay", *Invest New Drugs, Short Report*, 6 pages (2011).
Song et al., "Bisphosphonate inhibitors of ATP-mediated HIV-1 reverse transcriptase catalyzed excision of chain-terminating 3'-azido, 3'-deoxythymidine: A QSAR investigation", *Bioorg. Med. Chem.*, 16(19), 8959-8967 (2008).
Sturtz et al., "A study of the delivery-targeting concept applied to antineoplasic drugs active on human osteosarcoma. I. Synthesis and biological activity in nude mice carrying human osteosarcoma xenografts of gem-bisphosphonic methotrexate analogues", *Eur. J. Med. Chem.*, 27(8), 825-833 (1992).
Sturtz et al., "Synthesis of gem-bisphosphonic methotrexate conjugates and their biological response towards Walker's osteosarcoma", *Eur. J. Med. Chem.*, 28, 899-903 (1993).
Uludag et al., "Bisphosphonate Conjugation to Proteins as a Means to Impart Bone Affinity", *Biotechnol. Prog.*, 16, 258-267 (2000).
Vepsalainen, "Bisphosphonate Prodrugs", *Current Medicinal Chemistry*, 9, 1201-1208 (2002).
Vitha et al., "Complexes of DOTA—Bisphosphonate Conjugates: Probes for Determination of Adsorption Capacity and Affinity Constants of Hydroxyapatite", *Langmuir*, 24, 1952-1958 (2008).
Vogt et al., "Breast tumour growth inhibition in vitro through the combination of cyclophosphamide/methotrexate/5-fluorouracil, epirubicin/cyclophosphamide, epirubicin/paclitaxel, and epirubicin/docetaxel with the bisphosphonates ibandronate and zoledronic acid", *Oncology Reports*, 12, 1109-1114 (2004).
Widler et al. "Highly Potent Geminal Bisphosphonates.From Pamidronate Disodium (Aredia) to Zoledronic Acid (Zometa)", *J. Med. Chem.*, 45, 3721-3738 (2002).
Wingen et al., "Xynthesis, antitumor activity, distribution and toxicity of 4-[4-[Bis(2-chloroethyl)amino]phenyl]-1-hydroxybutane-1 1-bisphosphonic acid (BAD), a new lost derivative with increased accumulation in rat osteosarcoma", *J. Cancer Res. Clin. Oncol.*, 111, 209-219 (1986).
Winter et al., "Exploring the anti-tumour activity of bisphosphonates in early breast cancer", *Cancer Treatment Reviews*, 34, 453-475 (2008).
Winter et al., "Bisphosphonates in breast cancer: teaching an old dog new tricks", *Current Opinion in Oncology*, 21, 499-506 (2009).
Zhang et al., "'Magic bullets' for bone diseases: progress in rational design of bone-seeking medicinal agents", *Chem. Soc. Rev.*, 36, 507-531 (2007).

BONE-TARGETING BISPHOSPHONATE DUPLEX DRUGS

The present invention relates to novel bisphosphonate duplex drugs, methods for preparing said compound; pharmaceutical compositions containing the same; as well as the use of said compounds in human and veterinary medicine, and, in particular, for treating tumors, viral infections, or dental disorders.

TECHNICAL BACKGROUND

1-Hydroxybisphosphonates (BPs) are analogues of pyrophosphate where the P—O—P linkage is replaced by P—C—P. The carbon atom contains the 1-hydroxygroup and a variable side chain.[1] The P—C—P bond is relatively stable towards chemicals and enzymatic hydrolysis. The powerful binding affinity towards bones is used in medicine for treatment in bone resorption and other bone disorders such as osteoporosis or tumor-induced osteolysis.[2, 3] Bones are the most common sites for metastasis in patients with solid tumors arising from breast, prostate, lung, thyroid and kidney.[4] The use of BPs has had a profound beneficial effect on the management of metastatic bone disease and the prevention of treatment-induced bone loss.[5] BPs were also investigated for their potential use in parasital diseases.[6, 7] The BPs bind strongly to hydroxylapatite and have been suggested as a bone-targeting vector in various tissue-specific contrast agents.[8-12] Complexes of radioactive metal ions with BPs have been applied in bone cancer radiotherapy and in palliative settings for pain therapy associated with bone metastasis.[13] Approaches for a chemotherapeutic bone targeting of cytostatics or protein proposed the conjugation of methotrexate[14, 15], doxorubicine[16] or albumin[17] with BPs. Recent studies suggested that BPs have direct effects on tumor cells and may enhance the antitumor activities of cytostatics[18-27]. The potential usefulness of the BPs etidronate and zoledronate in decreasing or preventing inflammatory root resorption and replacement root resorption in replacement teeth was tested. Zoledronate was shown to prevent root resorption and to facilitate regeneration of periodontal tissues after replantation[40].

Therapeutic nucleoside analogues like 2'-deoxy-5-fluorouridine (5-FdU), arabinofuranosyl cytidine (araC) and azidothymidine (AZT) are well-known compounds and their activity as antiviral and antitumor drugs is well-established since many years. Bone-targeting of those compounds has not been suggested so far.

There is a continuous need for further drugs allowing the targeted treatment of bone-related disorders like, for example, of bone tumors or metastatic bone tumors.

SUMMARY OF THE INVENTION

The problem to be solved by the present invention is, therefore, the provision of a novel type of drugs suitable for bone targeting.

Said problem could, surprisingly, be solved by the provision of pyrimidine compounds specifically derivatized with bisphosphonates, as further described in more detail below and in the claims.

In particular, aminobisphosphonates (alendronate, parmidronate) were covalently linked in a three step synthesis, with protected and triazolylated derivatives of chemotherapeutical used nucleoside analoga (5-FdU, AZT, araC) by substitution of their triazolyl residue. From the deprotected and chromatographically purified reaction mixtures N⁴-[alkyl-(hydroxyphosphono)phosphonate]-cytosine nucleosides combining two differently antitumor active compounds were obtained.

The new kind of duplex drugs can make bone-targeting possible due to its bisphosphonate residue. It is expected that the metabolism of the duplex drugs will produce different cytostatic active compounds with additive or synergistic antitumor effect. Initial in vitro testing of multiple tumor cell lines with 1 5FdU-alendronate surprisingly showed variable growth inhibition of 11 tumor cell lines.

PARTICULAR EMBODIMENTS OF THE INVENTION

The present invention relates to the following particular embodiments:

1. A bisphosphonate of the general formula I

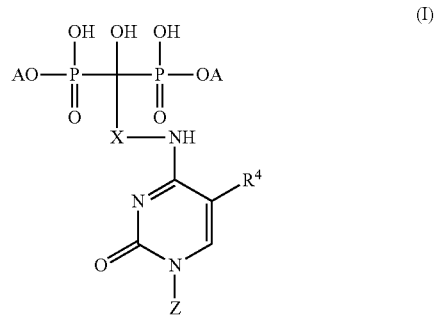

wherein the parameters independently of each other or in combination have the following meanings:
residues A independently of each other represent a proton or a monovalent metal cation;
X represents a straight-chain or branched alkylene, in particular $C_1$-$C_6$-alkylene, bridge;
Z represents H or a 5- or 6-membered carbo- or heterocyclic, in particular 5-membered heterocyclic, optionally mono- or poly-substituted ring, and
$R^4$ represents hydrogen, halogen, amino, hydroxy, trifluoromethyl, linear or branched alkyl linear or branched alkoxy, or bromovinyl; in particular hydrogen, halogen, or linear or branched alkyl.

2. The compound of embodiment 1 of the general formula Ia

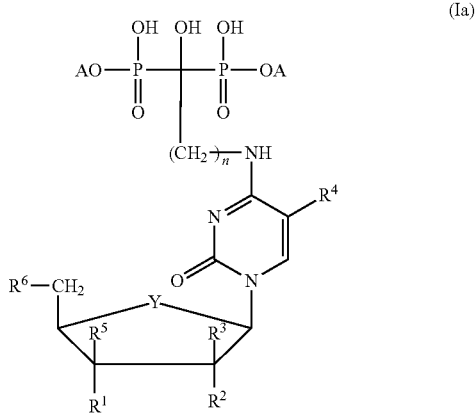

wherein the parameters independently of each other or in combination have the following meanings:
residues A independently of each other represent a proton, or a monovalent metal cation;
Y represents O or S, in particular O;
n represents an integer of 1, 2, 3 or 4, in particular 2 or 3;
$R^1$, $R^2$, $R^3$ and $R^5$ independently of each other represent hydrogen, halogen, fluoromethylene, hydroxy, azido, cyano, linear or branched alkoxyl, acyl, lower alkinyl, in particular hydrogen, hydroxy, halogen, azido, or lower alkinyl;
$R^4$ represents hydrogen, halogen, amino, hydroxy, trifluoromethyl, linear or branched alkyl, linear or branched alkoxyl or bromovinyl, in particular hydrogen, halogen, or linear or branched alkyl;
$R^6$ represents hydrogen, halogen, amino, hydroxy, phosphate, linear or branched alkyl, linear or branched alkoxyl or acyl, in particular hydroxy or acyl.

3. The compound of embodiment 2, wherein the parameters independently of each other or in combination have the following meanings:
residues A independently of each other represent a proton, or a alkali metal cation;
Y represents O;
n represents an integer of 2 or 3;
$R^1$ represents hydrogen, halogen, azido or hydroxy;
$R^2$ represents hydrogen or hydroxy;
$R^3$ represents hydrogen or hydroxy
$R^4$ represents hydrogen, halogen, or linear or branched alkyl;
$R^5$ represents hydrogen or lower alkinyl; and
$R^6$ represents hydroxy or acyl 4. The compound of embodiment 2 or 3, wherein the parameters independently of each other or in combination have the following meanings:
residues A independently of each other represent $Na^+$ or $K^+$;
Y represents O;
n represents an integer of 2 or 3;
$R^1$ represents azido or hydroxy;
$R^2$ represents hydrogen or hydroxy;
$R^3$ represents hydrogen or hydroxy
$R^4$ represents hydrogen, fluoro or methyl;
$R^5$ represents hydrogen or ethinyl; and
$R^6$ represents hydroxy.

5. A compound of anyone of the preceding embodiments for use in human and animal medicine.

6. A compound of anyone of the embodiments 1 to 4 for use in the treatment of tumours or viral infections.

7. A compound of anyone of the embodiments 1 to 4 for use in the treatment of bone tumours, including metastatic bone tumours.

8. A compound of anyone of the embodiments 1 to 4 for use in dental healing, in particular in the treatment or prevention of dental disorders, like inflammatory disorders, such as inflammatory root resorption or replacement root resorption in replanted teeth; or regeneration of periodontal tissue after tooth replantation; or in operative dentistry or oral surgery, in particular for tooth stabilization and tooth maintenance. For example, a compound of the present invention may be applied (for example topically) onto the tooth or the jawbone in order to stabilize tooth and/or bone tissue.

9. A pharmaceutical composition comprising in a pharmaceutically acceptable carrier at least one compound of anyone of the embodiments 1 to 4 optionally in combination with at least one further therapeutically active ingredient.

10. A method of preparing a compound of general formula I as defined in embodiment 1, which method comprises
a) reacting a compound of general formula II

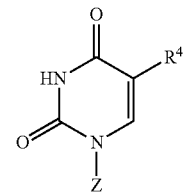

(II)

wherein Z and $R^4$ are as defined above, provided that if anyone of residues Z and $R^4$ contains a hydroxy group said hydroxy group is a protected hydroxy group,
with triazole to for a compound of formula III

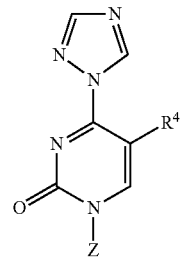

(III)

b) reacting a compound of formula III with an aminophosphonate of the general formula IV

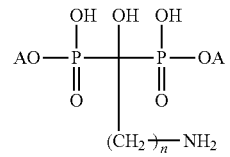

(IV)

c) and isolating the desired product optionally after removing any protecting groups.

11. A method of preparing a compound of general formula Ia as defined in anyone of the embodiments 2 to 4, which method comprises
a) reacting a compound of general formula IIa

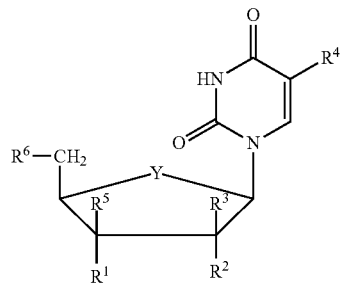

(IIa)

wherein Y and $R^1$, $R^2$, $R^3$, $R^4$, $R^5$ and $R^6$ are as defined above, provided that if anyone of residues $R^1$ to $R^6$ shall be hydroxy group said group is a protected hydroxy group,
with triazole to for a compound of formula IIIa

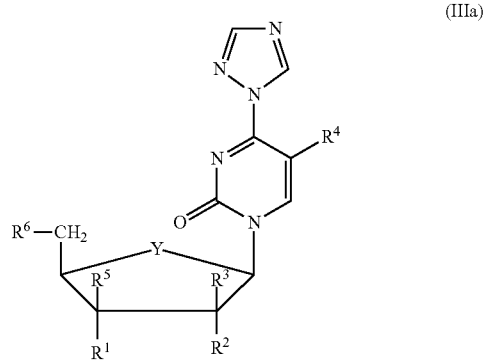

b) reacting a compound of formula IIIa with an aminophosphonate of the general formula IV

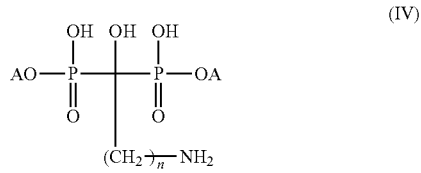

c) and isolating the desired product optionally after removing any protecting groups.

12. The method of embodiment 10 or 11, wherein the aminophosphonate compound is selected from alendronate and pamidronate.

DESCRIPTION OF FURTHER EMBODIMENTS AND ASPECTS OF THE INVENTION

1. Definitions

Unless otherwise stated the following definitions shall apply:

"Monovalent metal cations" comprise cations of alkali metals, in particular Na and K.

A "phosphonate" group is represented by the formula $(-PO_3)^{2-}$ (linked to a chemical compound); and comprises the corresponding protonated forms as well as salt forms with monovalent metal cations A "straight-chain or branched alkylene bridge" is a linear or branched bridging hydrocarbon group having 1, 2, 3, 4, 5 or 6 carbon atoms, and may also be designated as "$C_1$-$C_6$-alkylene" group. As examples of such groups may be mentioned: methylene, 1,2-ethylene, 1,2- and 1,3-propylene, 1,2-, 1,3-, 2,3- and 1,4-butylene, 1,5-pentylene, 1,6-hexylene and constitutional isomers thereof. In particular there may be mentioned: —CH$_2$—CH(Met)-, —CH(Met)-CH$_2$—, —CH(Met)-CH(Met)-, —C(Met)$_2$-CH$_2$—, —CH$_2$—C(Met)$_2$-, —C(Met)$_2$-CH(Met)-, —CH(Met)-C(Met)$_2$-, —CH$_2$—CH(Et)-, —CH(Et)-CH$_2$—, —CH(Et)-CH(Et)-, —C(Et)$_2$-CH$_2$—, —CH$_2$—C(Et)$_2$-, —CH$_2$—CH(n-Prop)-, —CH(n-Prop)-CH$_2$—, —CH(n-Prop)-CH(Met)-, —CH$_2$—CH(n-Bu)-, —CH(n-Bu)-CH$_2$—, —CH(Met)-CH(Et)-, —CH(Met)-CH(n-Prop)-, —CH(Et)-CH(Met)-, —CH(Met)-CH(Et)-, wherein Met is methyl, Et is ethyl, n-Prop is n-propyl and n-Bu is n-butyl.

As "linear or branched alkyl" there may be mentioned: $C_1$-$C_8$-alkyl radicals which are linear or branched radicals having from 1 to 8 carbon atoms. Examples thereof are the $C_1$-$C_4$-alkyl (also designated "linear or branched lower alkyl") radicals methyl, ethyl, n-propyl, isopropyl, n-butyl, 2-butyl, isobutyl or tert-butyl; and additionally pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl and their constitutional isomers such as 2-ethylhexyl; or $C_8$-$C_{30}$-alkyl radicals which are linear or branched radicals having from 8 to 30 carbon atoms. Examples thereof are octyl, nonyl, decyl, undecyl, dodecyl, tridecyl, tetradecyl, pentadecyl, hexadecyl, heptadecyl, octadecyl, nonadecyl, eicosyl, hencosyl, docosyl, tricosyl, tetracosyl, pentacosyl, hexacosyl, heptacosyl, octacosyl, nonacosyl, squalyl, their constitutional isomers, higher homologs and constitutional isomers thereof.

As "linear or branched alkoxyl" there may be mentioned the oxygen-linked, analogues of the above "linear or branched (lower)alkyl" residues.

An "acyl" group, is of the general Formula R—(C=O)— wherein R represents a saturated or mono- or poly-unsaturated $C_{1-30}$-hydrocaron residue. In particular, said residue is a straight-chain mono- or poly-unsaturated hydrocarbon residue or a mixture of such residues with an average length of 1-30, 1-29, 1-10, 1-5 or 5-25 carbon atoms. Particularly preferred residues are:

residues derived from saturated, straight-chain carboxylic acids: $CH_3$—, $C_2H_5$—; $C_3H_7$—; $C_4H_9$—; $C_5H_{11}$—; $C_6H_{13}$—; $C_7H_{15}$—, $C_8H_{17}$—; $C_9H_{19}$—; $C_{10}H_{21}$—; $C_{11}H_{23}$—; $C_{12}H_{25}$—; $C_{13}H_{27}$—; $C_{14}H_{29}$—; $C_{15}H_{31}$—; $C_{16}H_{33}$—; $C_{17}H_{35}$—; $C_{18}H_{37}$—; $C_{19}H_{39}$—; $C_{20}H_{41}$—; $C_{21}H_{43}$—; $C_{23}H_{47}$—; $C_{24}H_{49}$—; $C_{25}H_{51}$—; $C_{29}H_{59}$—; $C_{30}H_{61}$;

residues derived from saturated, branched carboxylic acids: iso-$C_3H_7$—; iso-$C_4H_9$—; iso-$C_{18}H_{37}$—;

residues derived from mono-unsaturated, straight-chain carboxylic acids: $C_2H_3$—; $C_3H_5$—; $C_{15}H_{29}$—; $C_{17}H_{33}$—; $C_{21}H_{41}$—;

residues derived from two-fold unsaturated, straight-chain carboxylic acids: $C_5H_7$—; $C_{17}H_{31}$—;

residues derived from three-fold unsaturated, straight-chain carboxylic acids: $C_{17}H_{29}$—;

residues derived from four-fold unsaturated, straight-chain carboxylic acids: $C_{19}H_{31}$—;

residues derived from five-fold unsaturated, straight-chain carboxylic acids: $C_{21}H_{33}$—

A "lower alkinyl" group comprises $C_2$-$C_4$-alkinyl radicals which are linear or branched, in particular llinear, hydrocarbon radicals having from 2 to 4 carbon atoms and one C—C triple bond, as for example ethinyl, 1- or 2-propinyl, and 1-, 2- and 3-butinyl.

As "5- or 6-membered carbo- or heterocyclic ring" there may be mentioned a "mono- or bicyclic ring", optionally condensed residue, which may be a non-aromatic or aromatic or heteroaromatic ring, having 3 to 12 ring carbon atoms and optionally 1 to 4 heteroatoms, like N, S and O. As examples there may be mentioned cyclopropyl, cyclobutyl, cyclopenty, cyclohexyl, cycloheptyl, as well as the mono- or polyunsaturated analogues thereof, as for example cyclobutenyl, cyclopentenyl, cyclohexenyl, cycloheptenyl, cyclohexadienyl, cycloheptadienyl; naphthyl and phenyl; as well as 5- to 7-membered saturated on mono- or polyunsaturated heterocyclic radicals having 1 to 4 heteroatoms, selected from O, N and S, and wherein the heterocyclic ring may be further condensed with another heterocyclic or carbocyclic ring. Example of heterocyclic residues are those derived from pyrrolidine, tetrahydrofurane, piperidine, morpholine, pyrrole, furane, thiophene, pyrazole, imidazole, oxazole, thiazole, pyridine, pyrane, purine, pyrimidine, pyridazine, pyrazine, coumarone, indole and quinoline. In particular the ring group is a pyrimindine-type structure, like preferably a cytosine, thymine or uracil ring.

"Optionally mono- or poly-substituted" means substitution with at least one of the following substituents: $NH_2$, OH, Keto (C=O), SH, halogen, like F, Cl, Br, J; lower alkoxy, lower alkyl or lower alkinyl as defined above.

As "halogen" residues there may be mentioned residues of F, Cl, Br and I.

2. Particular Duplex Drugs

As non-limiting examples of particular duplex drugs of the general formula I or Ia there may be mentioned:

Alendronate-Type Duplexes.
$N^4$-[butyl-(4-hydroxy-4-phosphono)phosphonate]-5-fluoro-2'-deoxycytidine (5-FdU-alendronate) (6a)
$N^4$-[butyl-(4-hydroxy-4-phosphono)phosphonate]-1-(β-D-arabinofuranosylcytosine (araU-alendronate) (6b).
$N^4$-[butyl-(4-hydroxy-4-phosphono)phosphonate]-5-methyl-3'-azido-2'3'-dideoxycytidine (AZT-alendronate) (6c).

Pamidronate-Type Duplexes:
$N^4$-[propyl-(3-hydroxy-3-phosphono)phosphonate]-5-fluoro-2'-deoxy-cytidine (5-FdU-pamidronate) (7a)
$N^4$-[propyl-(3-hydroxy-3-phosphono)phosphonate]-1-β-D-arabinofuranosylcytosine (araU-pamidronate) (7b)
$N^4$-[propyl-(3-hydroxy-3-phosphono)phosphonate]-5-methyl-3'-azido-2',3'-dideoxycytidine (AZT-pamidronate) (7c)

3. Pharmaceutical Formulations and Uses According to the Invention

The invention also relates to pharmaceutical agents, containing at least one duplex compound according to the above definition in a pharmaceutically compatible vehicle or diluent, such as for example contained in liposomes or nanoparticles.

The compounds according to the invention are generally used in the form of pharmaceutical agents for the treatment of an individual, preferably a mammal, in particular a human being. Thus, the compounds are usually administered in the form of pharmaceutical compositions, which comprise a pharmaceutically compatible excipient with at least one nucleoside bisphosphonate analog according to the invention, optionally also a mixture of several compounds according to the invention, and optionally other active substances that can be used for the respective desired therapeutic effect. Said compositions can for example be administered by the oral, rectal, transdermal, subcutaneous, intravenous, intramuscular or intranasal route or topically.

Examples of suitable pharmaceutical formulations are solid pharmaceutical forms, such as powders, granules, tablets, pastilles, sachets, cachets, dragées, capsules such as hard and soft gelatin capsules, suppositories or vaginal pharmaceutical forms; semi-solid pharmaceutical forms, such as ointments, creams, hydrogels, pastes or plasters, and liquid pharmaceutical forms, such as solutions, emulsions, in particular oil-in-water emulsions, suspensions, for example lotions, preparations for injection and infusion, eye and ear drops. Implanted delivery devices can also be used for administration of the compounds according to the invention. Liposomes, microspheres or polymer matrixes can also find application.

For production of the pharmaceutical agents, compounds according to the invention are usually mixed or diluted with an excipient. Excipients can be solid, semi-solid or liquid materials, which serve as vehicle, carrier or medium for the active substance.

Suitable excipients include for example lactose, dextrose, sucrose, sorbitol, mannitol, starches, acacia gum, calcium phosphate, alginates, tragacanth, gelatin, calcium silicate, microcrystalline cellulose, polyvinylpyrrolidone, cellulose, water, syrup and methylcellulose. The formulations can also comprise pharmaceutically acceptable vehicles or usual excipients, such as glidants, for example tallow, magnesium stearate and mineral oil; wetting agents; emulsifying and suspending agents; preservatives, such as methyl- and propylhydroxybenzoates; antioxidants; antiirritants; chelating agents; sugar-coating aids; emulsion stabilizers; film-forming agents; gelling agents; odor-masking agents; flavor correctants; resins; hydrocolloids; solvents; solubilizers; neutralizing agents; permeation accelerators; pigments; quaternary ammonium compounds; refatting and overfatting agents; bases for ointments, creams or oils; silicone derivatives; spreading aids; stabilizers; sterilizing agents; bases for suppositories; tableting excipients, such as binders, fillers, glidants, disintegrants or coatings; propellants; drying agents; opacifiers; thickeners; waxes; plasticizers; white oils. An embodiment in this respect is based on expert knowledge, as described for example in Fiedler, H. P., Lexikon der Hilfsstoffe für Pharmazie, Kosmetik und angrenzende Gebiete (Encyclopedia of excipients for pharmacy, cosmetics and related areas), 4th edition, Aulendorf: ECV-Editio-Kantor-Verlag, 1996.

Particular usual vehicles are for example mannitol, glucose, dextrose, albumins or the like; preferred diluents are essentially physiological saline or a 5% glucose solution. Furthermore, it is usual to buffer such solutions with suitable reagents.

For better application of the compounds according to the invention, compositions can be provided that contain the compounds according to the invention in combination with an organic vehicle. Furthermore, any other excipients that are usually employed for the preparation of pharmaceutical agents can be added, provided proper use of said composition of organic vehicle and the compounds according to the invention is not impaired.

A preferred embodiment of such compositions envisions the association of the compounds according to the invention in the form of uni- to oligolamellar liposomes with a diameter of max. 0.4 µm. All methods of liposome preparation that are known per se can be used for forming the liposomes, for example ultrasound, gel chromatography, detergent analysis, high-pressure filtration.

The pharmaceutical compositions of the invention may include a "therapeutically effective amount" or a "prophylactically effective amount" of a compound of the invention. A "therapeutically effective amount" refers to an amount effective, at dosages and for periods of time necessary, to achieve the desired therapeutic result. A therapeutically effective amount of the compound may vary according to factors such as the disease state, age, sex, and weight of the individual, and the ability of the compound to elicit a desired response in the individual. A therapeutically effective amount is also one in which any toxic or detrimental effects of the compound are outweighed by the therapeutically beneficial effects.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a compound of the invention is 0.01-600 mg/kg, more particular 0.1-200 mg/kg, 0.5-150 mg/kg, or 1-90 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Furthermore, compositions according to the invention may additionally contain at least one other pharmacological active substance, which is suitable for the treatment of infectious diseases and/or cancers.

We may mention, as non-limiting examples of other active substances for tumor treatment:
(A) Antineoplastic agents, such as
  (1) phytocytostatics, e.g. mistletoe preparations,
  (2) chemically defined cytostatics, such as
    a) alkaloids and podophyllotoxins, for example vinblastin, vincristin and other vinca alkaloids and analogs; podophyllotoxin derivatives, such as etoposide;
    b) alkylating agents, such as nitrosoureas and nitrogen mustard analogs, for example cyclophosphamide and estramustine;
    c) cytotoxic antibiotics, such as anthracyclines and related substances, for example daunorubicin, doxorubicin; bleomycin and mitomycin;
    d) antimetabolites, such as folic acid analogs, for example methotrexate, purine analogs, pyrimidine analogs, for example gemcitabine and 5'-fluorouracil;
  (3) platinum compounds, such as carboplatin, cisplatin;
  (4) enzymes and monoclonal antibodies;
  (5) endocrine-active antineoplastics, such as
    a) hormones and related substances, for example estrogens, gestagens, for example medroxyprogesterone acetate; hypothalamus hormones, such as gonadorelin analogs, for example buserelin;
    b) hormone antagonists, such as the antiestrogen tamoxifen and other antiestrogens; or the antiandrogen flutamide and other antiandrogens;
    c) enzyme inhibitors
(B) Protective agents/antidotes for antineoplastic therapy, e.g. folinic acid.

As nonlimiting examples of other active substances for the treatment of infectious diseases, such as in particular AIDS, we may mention: azidothymidine, dideoxycytidine, sanilvudine, stavudine (1-(2,3-d ideoxy-beta-D-glycero-pent-2-enofuranosyl)-5-methyl-2,4(1H,3H)-pyrimidinedione), dideoxyinosine, recombinant (human) interleukin-2, saquinavir mesylate, interferon alpha, nevirapine, abacavir sulfate, CD4-immunoadhesin, lamivudine, kynostatin-272, emtricitabine, delavirdine mesylate, HIV-1-immunogen, indinavir sulfate, azidothymidine phosphonate, calanolide A, amprenavir, efavirenz, ritonavir, nelfinavir mesylate, gadolinium texaphyrin, enfuvirtide, buffy coat interleukin, semapimod hydrochloride, elvucitabine, canovirin N, tipranavir, azodicarbonamide, tenofovir disoproxil fumarate, atazanavir sulfate, lamivudine/zidovudine, sampidine, dapivirine, etravirine, lopinavir/ritonavir, adargileukin-alpha, glyminox, ancriviroc, O-(2-hydroxypropyl)-beta-cyclodextrin, darunavir, maraviroc, abacavir sulfate/lamivudine, sulfonated hesperidin, rilpivirin, tenofovir, In particular the invention also relates to the use of at least one compound according to the above definition for the production of a pharmaceutical agent for the prevention and/or therapy of infectious diseases and/or cancers, i.p. bone tumors and metastatic bone tumors.

4. Synthesis Concept of Antimetabolite Bisphosphonate Duplex Drugs

4.1 General

For the activity of BPs the P—C—P structure is a prerequisite and the intensity of the effects being exquisitely dependent upon the side chain. Small changes in the structure can lead to extensive alterations in their physiochemical, biological therapeutic and toxicological characteristics. The length of the lateral chain is very important. Highly active BPs contain side chains with terminal nitrogen atoms in form of amino groups or heterocyclic residues.[1] For example pamidronate with its 3-aminopropyl side chain has an about 10-fold lower activity than alendronate having a 4-aminobutyl side chain. The replacement of the terminal amino group by an imidazole residue resulting in Zoledronate (Zometa®) improved drastically the activity in respect to pamidronate and alendronate[2] and shows higher antitumor activities.

The coupling of pamidronate or alendronate to a cytostatic nucleoside analogue (antimetabolite) results in duplex drug. A target delivery of the duplex drug to bone or bone marrows will be possible due to BPs component. The antitumor effect of the linked cytostatic antimetabolites should be reinforced additively or synergistically by the activity of the cytostatic BPs component. The conjugation of BPs with virostatic antimetabolites results in a new antiviral duplex drug whose BPs component could inhibit the ATP-mediated HIV-1 reverse transcriptase catalyzed excision of chain-terminating AZT as proposed in literature.[28]

2'-deoxy-5-fluorouridine (5-FdU), 1-β-D-arabinofuranosyluracil (araU) and AZT were chosen as antimetabolites on a pyrimidine nucleoside basis for the synthesis of the duplex drugs. The coupling of nucleoside analogues via an esterification of its hydroxy group with the phosphonate groups of the BPs as described for 3'-Azido-2',3'-dideoxythymidine (AZT)[29] and other nucleosides[30] did not seem to us to be best. It cannot be excluded, that the esterification with only one phosphonate group could reduce the high affinity of BPs to bone. Several mono-, di-, tri- and tetraesters of BPs were ineffective prodrugs of the parent BPs[2]. Free geminal BPs showed the highest affinities for the surface of hydroxylapatite.[13] We have therefore developed another concept for the coupling of nucleosides and selected BPs, in which the BP-terminal phosphonates groups will not be derivatized. In analogy to previously described synthesis[31-33], aminobisphosphonate were attached via their terminal amino groups by substitution of the triazolyl residue of uracil nucleosides derivatives which was prior induced at the 4-position of the nucleobase resulting in N4-[alkyl-(hydroxyphosphono)phosphonate]-cytosine nucleosides analogues. The synthesis is not limited to the examples described here, but may also be used for conjugation of other pyrimidine antimetabolites such as gemcitabine and 3'-ethinylcytidine.

4.2 Synthesis of Preferred Duplex Drugs

A suitable synthesis route of compounds of the invention is illustrated for $N^4$-[alkyl-(hydroxyphosphono)phosphonate]-cytosine nucleosides in the following scheme:

$N^4$-[alkyl-(hydroxyphosphono)phosphonate]-cytosine nucleosides were prepared in three steps starting with uridine analoga (1). In the first synthesis step the free carbohydrate hydroxyl groups of 1 were protected with acetyl residues resulting in 2 in 94%-97% yields. Acetylated 5-FdU (2a) was obtained as crystalline solid, the acetylation of AZT resulted in a solid foam. In the second step the 1,2,4-triazolyl residue was introduced in the 4-position of the protected uracil resi-

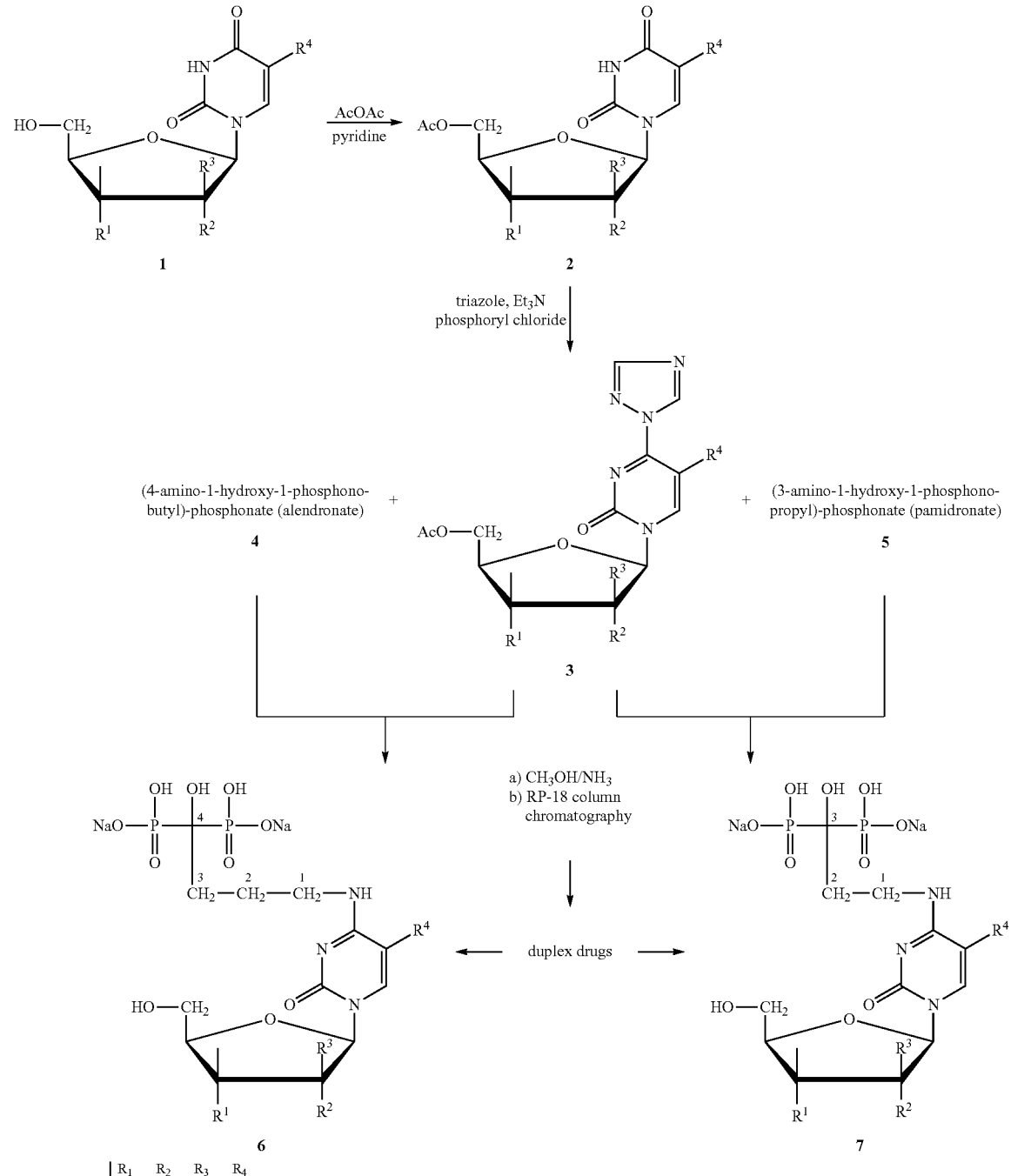

|  | $R_1$ | $R_2$ | $R_3$ | $R_4$ |
|---|---|---|---|---|
| 1a, 6a, 7a | OH | H | H | F |
| 1c, 2c, 3c, 6c, 7c | $N_3$ | H | H | $CH_3$ |
| 2a, 3a | OAc | H | H | F |
| 2b, 3b | OAc | OAc | OAc | H |
| 1b, 6b, 7b | OH | OH | OH | H | dues. The O-acetylated and 4-triazolylated uridine analogues 3 were obtained in yield between 77% 3c and 88% 3a. 3b was synthesized according to published methods.[31] The triazolyl residue of 3 was substituted in the third synthesis step by (amino-1-hydroxyphosphono)phosphonates (alendronate (4), pamidronate (5) using equimolar amount of nucleoside and BPs resulting in acetylated $N^4$-[alkyl-(hydroxyphosphono)phosphonate]-cytosine nucleoside. The unfavorable equimolar ratio of the reaction partners in respect to a desired high yield of duplex drugs was chosen as the separation of the hydrophilic duplex drug from an excess of unreacted also hydrophilic BPs will be difficult. The course of the substitution was monitored by TCL. During the reaction the flourescencing spot (360 nm) of 3 disappeared and new slower migrating dark spots (254 nm) and the desired duplex drug remaining as a dark spot at the origin were formed. The isolation and purification of the acetylated duplex drug was achieved in two steps. At first the main part of the desired product precipitated together with the unreacted BPs and a small amount of side products by adding $CH_3OH$ to the sirup obtained after concentration of the reaction mixture and was filtered of. The obtained and partially purified residue was dissolved in ammonia and kept at room temperature to remove the acetyl protecting groups. The rest of the desired reaction product was chromatographically obtained from the filtrate using RP-18 reversed phase column and afterwards deprotected.

The chromatographic separation was rendered more difficult because the retention time of the duplex drug and the unreacted BPs were very similar. Using only water as the eluent the BPs leave the column at first immediately followed by the duplex drug whereas the uncoupled nucleosidic components and side products remained at the column. Duplex drugs were UV-detectable at 254 nm, whereas the BPs were UV-inactive and not detected when the eluate was automatically scanned by UV-detector. The concentrated and lyophilised eluent containing the duplex drugs resulted in white powders of differently hydratisated 6 and 7.

A possible alternative chromatographic purification using anion exchanger column which was normally used to separate nucleotides[34] would drastically increase the retention time of the negative charged compounds. The longer retention would not improve the resolution of the elution profile. Beside this, the necessary eluent for anion exchange chromatography contain salt which has to be removed from the eluated compounds in a time consuming procedure. The difficult purification of the reaction mixture could be one reason that the analytical pure duplex drugs were only obtained in low yields ranging between 35% and 55%. Another reason could be the unfavorable reaction conditions for the substitution. The solubility of the polar BPs being only soluble in water in respect to their of the protected unpolar nucleoside derivatives which were nearly insoluble in water is not a good requirement for a homogenous reaction. The used reaction medium of water/DMSO was not a suitable reaction environment favoring the substitution in high yield. Analogue substitutions using amino components being soluble in organic solvents resulted in 95% yield.[33]

A reversible esterification of the phosphonate residue of the BPs improve its solubility in organic solvent and could increase the yield of the substitution, however, the effort of these reversible protection would also drastically increase the synthesis effort. The chemical structure and the analytical purity of the synthesis products were confirmed by NMR-mass spectroscopy and elementary analysis. Elementary analysis of 2c and 3a were not performed because these substances were only obtained as syrup or foam.

5. Antitumor Activities of the Duplex Drugs 5.1 In Vitro Anticancer Activity of 5-FdU-Alendronate (6a)

Initial evaluations concerning the in vitro cytostatic activity of the duplex drugs was so far only performed with 5-FdU-alendronate (6a) using the 60-cell line in vitro screening tests of the National Cancer Institute (NCI, USA). In these screens the growth percent caused by a short 48 h incubation using only one dose (10 µM) of 5-FdU-alendronate was determined (additional details of the NCI screen can be found at http://www.dtp.nci.nih.gov). Under these conditions the growth of 11/59 tested cell lines was reduced in the range between 95% and 62% whereas the other cell lines (48/59) did not show any growth inhibition. The 11 sensitive cell lines are listed in table 1. The low cytostatic effect, which was found in the NCI screen is probably due to the short incubation period (48 h) and the low dose. In this short incubation time, the duplex drug was probably not sufficiently metabolized, so that the concentration of cytostatic metabolites was not sufficient for effective growth inhibition. Despite this probably too short incubation period, it was already noticed a different sensibility concerning growth of the tested tumor cell lines. This orientating inhibition data showed already that the duplex drugs represent a new BP with a comparable anticancer activity to standard BPs as shown in the following published examples. 6 different tumor cell lines tested with the ATP-based tumor chemosensitivity assay show a 50% growth inhibition after 6 days of incubation if in average 1-1406 µM Clondronat, 11-1856 µM Alendronat or 2-1912 µM Zoledronic acid were added.[21] In another examination Zoledronic acid showed on average a better effectiveness in 8 other cell lines, whose sensibility was evaluated with the MTT assay. For 50% growth of these cell lines inhibition a dose of only 2.3-86.6 µM Zoledronic acid was needed.[18] More detailed studies on the cytostatic potential and bone targeting of the duplex drugs are necessary and currently in progress.

5.2 Possible Causes and Mechanism Resulting in Antitumor Activities

The two drugs combined in a duplex drug molecule have two different cytostatic functions. On the one hand the cytostatic or antiviral active nucleoside and on the other hand the cytostatic BPs residue. It is therefore conceivable that even the intact whole molecule can be active. As an example of an active drug with a dual function a conjugate of Iost and BP has been described.[35] In contrast, a coupling of the cytostatic drug Doxorubicin with BPs to a Doxorubicin-conjugate had no cytostatic effect against human tumor xenografts.[16]

It can be estimated that the duplex drug could be a prodrug that can be degraded into a mixture of different cytostatic metabolites. In the case that the relatively labile N-glycosidic bond between the carbohydrate and nucleobase is enzymatically cleaved, new, previously undescribed N-containing BPs result, whose alkyl chain show terminally a pyrimidinone—(from araU), 5-fluoropyrimidinone (from 5-FdU) or a 5-methylpyrimidinone (from AZT) residue. The hydrolytic cleavage at the much more stable N4-position can lead to amino-BPs and respective uracil nucleosides (5-FdU, AraU, AZT). This pathway would result in a mixture of drugs with expected particularly high antitumor effects. The cytostatic effects of the formed metabolites could be caused by the fact that on the one hand the antimetabolites disrupt the functions of DNA and RNA. On the other hand the cytostatic mechanism of N-BPs by BPs-induced ATP-analog formation was proposed[36].

It is known that with the aid of the BP function a bone targeting becomes possible, as shown by the described bone targeting ability of 3-(1',1'-ethylbisphosphonates)-5-fluorouracil.[37] The relatively stable anchoring of the BPs to the $N^4$-position of cytosine may contribute to the accumulation of duplex drug in the bone before its complete metabolisation and therefore it could act as a 5FdU-depot enriched in metastatic bones.

The invention will be further explained by making reference to the following non-limiting examples.

EXPERIMENTAL PART

A. General Chemistry

Unless otherwise noted, starting materials were purchased from commercial sources and were used as is. 3'-Azido-2',3'-dideoxythymidine (AZT, 1c) was isolated from expired drugs,[29],[38] 4-(1,2,4-triazol-1-yl)-1-(β-D-2',3',5'-tri-O-acetyl-arabinofuranosyl)pyrimidine-2(1H)one (3b) was synthesised according to published methods.[31] (4-Amino-1-hydroxy-1-phosphonobutyl)phosphonate monosodium salt*3H$_2$0 (alendronate) (4) and (3-amino-1-hydroxy-1-phosphonopropyl)phosphonate monosodium salt*H$_2$0, (pamidronate) (5) were synthesised, as described, however, markedly lower yield were obtained.[39] The nucleoside derivatives and impurities were detected using UV-light and spray reagents as developing agents as previously describes.[33] TLC was performed on pre-coated silica gel plates 60$_{F254}$ (0.25 mm, Merck). Preparative column chromatography of the obtained mixtures (>2 g) was carried out at room temperature by flash chromatography on self-packed RP-18 reversed phase (LiChroprep, 40-60 μm) columns. The desired compounds were identified using UV-absorption. The eluate was collected in 20 ml fractions. The fractions of the desired product were concentrated to sirup and the product precipitated by adding MeOH. Smaller amounts (<2 g) were chromatographed using commercial available RP-18 reversed phase columns (Lobar B, LiChroprep RP-18 40-63 μm, Merck). The eluted product was isolated by lyophilisation of the combined fractions. Aliquots of the duplex drugs were purified to p.a. quality by twofold reversed phase chromatography and lyophilisation of the collected fractions. The concentration of the reaction mixtures, organic layers and eluted fractions were done in vacuo at a bath temperature of about 45° C. $^1$H and $^{13}$C-NMR spectra were obtained on a Bruker A 250 spectrometer at 250 and 62.9 MHZ or on a Bruker Avance 400 spectrometer at 400 and 100 MHZ, respectively. CDCl$_3$, and D$_2$O were used as solvents and Me$_4$Si as internal standard. $^{31}$P-NMR data were obtained on a Bruker Avance 400 spectrometer at 161 MHz, using H$_3$PO$_4$ as the external standard. Mass spectra were measured on a Finnigan TSQ 70 or on a Finnigan MAT 95 instrument. For FAB Mass spectra, all compounds were measured in a NBA or glycerine matrix.

B. Synthesis Examples

Synthesis of N$^4$-[alkyl-(hydroxyphosphono)phosphonate]-cytosine nucleosides

Example 1

Synthesis of Triazolyl-Intermediates (3)

1.1 Synthesis of 5-fluoro-4-(1,2,4-triazol-1-yl)-1-(β-D-3',5'-di-O-acetyl-2'-deoxy-ribofuranosyl)-pyrimidine-2(1H)-on (3a)

2'-Deoxy-5-fluorouridine (1a) (24.6 g, 0.1 mol) was dissolved in dry pyridine (200 ml) and acetic anhydride (47 ml, 0.5 mol) was added. The resulting solution was stirred under exclusion of moisture for 8 h at room temperature and subsequently concentrated until the crystallisation occurs. The concentrate was coevaporated with toluene (100 ml). The resulting residue was dissolved by heating (60° C.) in ethanol (250 ml) and re-crystallised standing overnight in a refrigerator. The precipitate was filtered, washed with cold ethanol and dried to yield 32.4 g (97%) of 3',5'-di-O-acetyl-2'-deoxy-5-fluorouridine; mp: 151° C.; R$_F$=0.35 (CHCl$_3$/MeOH, 95:5, v/v); MS (FAB$^+$) 331. $^1$[M-H$^+$]. Anal. calcd C$_{13}$FH$_{15}$N$_2$O$_7$ (330.3): C, 47.28; H, 4.58; N, 8.48. Found: C, 47.43; H, 4.78; N, 8.20. $^1$H-NMR (250 MHz, CDCl$_3$): δ=2.13 (s, 3H, —CH$_3$), 2.15 (s, 3H, —CH$_3$), 2.16-2.25 (m, 1H, H2'α), 2.55 (ddd, 1H, J1=2.3 Hz, J2=5.7 Hz, J3=14.3 Hz, H2'β), 4.28 (m, 1H, H4'), 4.32 (dd, 1H, J1=3.1 Hz, J2=12.2 Hz, H5'β), 4.41 (dd, 1H, J1=3.6 Hz, J2=12.1 Hz, H5'α), 5.24 (m, 1H, H3'), 6.31 (m, 1H, H1'), 7.7 (d, 1H, J=6.2 Hz, H6).

$^{13}$C-NMR (62.9 MHz, CDCl$_3$): δ=20.8 (COCH$_3$), 20.9 (COCH$_3$), 37.8 (C2'), 63.8 (C5'), 73.9 (C3'), 82.5 (C4'), 85.4 (C1'), 123.2 (d, J$_{CF}$=34.5 Hz, C6), 139.7 and 142.1 (d, J$_{CF}$=238 Hz, C5), 149.2 (C2), 156.9 (d, J$_{CF}$=26.7 Hz, C4), 170.3 (C=O), 170.5 (C=O).

1,2,4-Triazole (34.5 g, 0.5 mol) was dissolved under stirring and heating in dry acetonitrile (150 ml). The mixture was cooled to 10° C. under vigorous stirring and to the resulting suspension phosphoryl chloride (10.3 ml, 0.11 mol) was added dropwise that the temperature not increased over 25° C. Afterwards the reaction mixture was cooled again to ca. 10° C. and triethylamine (70 ml, 0.5 mol) was added dropwise under stirring that temperature not exceeded 20° C. To the again cooled (ca 10° C.) mixture 3',5'-di-O-acetyl-5-fluorouridine (2a) (16.5 g, 50 mmol) dissolved in dry acetonitrile (90 ml) was slowly added and the reaction mixture was stirred at ambient temperature for 4 h. After the addition of triethylamine (70 ml) and water (17 ml) the solution was concentrated to a sirup which was diluted with CHCl$_3$ (150 ml) and extracted with 5% sodium hydrogen carbonate solution (2×50 ml). The organic layer was concentrated and dried resulting in the crude product (16.7 g, 88%) of 3a as a solid foam which was used in the following synthesis step without further purification. R$_F$=0.35 (CHCl$_3$/MeOH, 95:5, v/v). The R$_F$ values 2a and 3a are very similar. 3a shows under UV-light (366 nm) violet fluorescence, whereas 2a is fluorescence inactive and appears as dark spot (254 nm) on the TLC plate. MS (FAB$^+$) 382.1 [M-H$^+$];

$^1$H-NMR (250 MHz, CDCl$_3$): δ=2.13 (s, 3H, COCH$_3$), 2.14 (s, 3H, COCH$_3$), 2.10-2.15 (m, 2H, H2'), 2.30 (dt, 1H, J1=6.7 Hz, J2=14.5 Hz, H2'α), 2.90, (ddd, 1H, J1=3.3 Hz, J2=5.9 Hz, J3=14.5 Hz, H2'β), 4.25-4.50 (m, 3H, H5'+H4'), 5.26 (m, 1H, H3'), 6.24 (dd, 1H, J1=6.1 Hz, J2=6.5 Hz, H1'), 8.25 (s, 1H, N=CH—N), 8.48 (d, 1H, J=6.5 Hz, H6), 9.25 (s, 1H, NCH—N). $^{13}$C-NMR (62.9 MHz, CDCl$_3$): δ=22.7 (COCH$_3$), 22.8 (COCH$_3$), 38.9 (C2'), 63.3 (C5'), 73.3 (C3'), 83.5 (C1'), 88.1 (C4'), 133.8 (d, J$_{CF}$=34.8 Hz, C6), 135.0, 137.5, 140.8 (d, J$_{CF}$=237 Hz, C5), 145.0 (NCN), 151.5, 154.8 (C2), 156.9 (d, J$_{CF}$=26.5 HZ, C4), 170.2 (C=O), 170.3 (C=O)

1.2 Synthesis of 5-methyl-4-(1,2,4-triazol-1-yl)-1-(β-D-5'-O-acetyl-3'-azido-2',3'-dideoxyribo-furanosyl)-pyrimidine-2(1H)-on (3c)

2'-Azido-2',3'-dideoxythymidine (1c) (9 g, 34 mmol) was dissolved in dry pyridine (70 ml). Acetic anhydride (16 ml, 0.17 mol) was added and the solution was stirred under exclusion of moisture for 8 h at ambient temperature, subsequently concentrated to a sirup, which was coevaporated with toluene (40 ml). After drying the sirup was obtained as a solid foam (9.8 g, 94%) of 5'-acetyl-2'-azido-2',3'-dideoxythymidine (2c) used without further purification in the following triazolylation, which was performed in analogy to 3.2.2 using 2c (9.8 g, 32 mmol) instead of 2a. The organic layer obtained after the neutralisation of the reaction mixtures was concentrated to a sirup. After the addition of ethanol (120 ml) the solution was concentrated to ca. 50 ml and kept overnight in a refrigerator (ca. 6° C.). The crystalline precipitate was removed by filtration, washed with a small amount of cold ethanol and dried resulting in 8.8 g (77%) of 3c. mp: 142-143° C. $R_F$=0.49 (CHCl$_3$/MeOH, 95:5, v/v); MS (FAB$^+$) 361 [M-H$^+$]. Anal. calcd. C$_{14}$H$_{16}$N$_8$O$_4$ (360.33): C, 46.66; H, 4.48; N, 31.10. Found: C, 46.72; H, 4.58; N, 31.65. $^1$H-NMR (250 MHz, CDCl$_3$): δ=2.16 (s, 3H, CH$_3$), 2.49 (s, 3H, CH$_3$), 2.43-2.55 (m, 1H, H2'), 2.81 (dt, 1H, J$_1$=6.4 Hz, J$_2$=14.1 Hz, H2'b), 4.14-4.28 (m, 2H, H3' and H4'), 4.40 (dd, 1H, J1=3.1 Hz, J2=12.4 Hz, H5'α), 4.50 (dd, 1H, J1=4.1 Hz, J2=12.4 Hz, H5'β), 6.15 (dd, 1H, J1=4.8 Hz, J2=6.5 Hz, H1'), 8.1 (s, 1H, NCHN), 8.13 (s, 1H, NCHN), 9.28 (s, 1H, H6). $^{13}$C-NMR (62.9 MHz, CDCl$_3$): δ=16.9 (CH$_3$), 20.5 (COCH$_3$), 38.3 (C2'), 59.5 (C5'), 62.7 (C3'), 82.6 (C1'), 87.5 (C4'), 105.3 (C5), 144.7 (C6), 145.8 (2xNCN), 153.2 (C2), 158.0 (C4) 169.9 (C=O)

Example 2

Synthesis of Bisphosphonate-Duplex Drugs (6), (7)

2.1 Synthesis of N$^4$-[butyl-(4-hydroxy-4-phosphono)phosphonate]-5-fluoro-2'-deoxycytidine (5-FdU-alendronate) (6a)

To a stirred and heated (85° C.) suspension of 4 (16.2 g, 50 mmol) in water (90 ml), 3a (19 g, 50 mmol), dissolved in dioxane, was added. The pH value of the suspension was adjusted between 8 and 9 by successively adding triethylamine. The progress of the substitution reaction was monitored by TLC. The fluorescence spot of the triazolyl compound (3a) disappears during the reaction and new, slower migrating fluorescent spots were formed. When the substitution was completed (ca. 3-4 h) the reaction mixture was allowed to cool down at room temperature. Unsolved compounds were removed by filtration and the filtrate was evaporated. To the obtained sirup MeOH (150 ml) was added and the formed fine precipitate was filtered of and dried resulting in the raw material I. The filtrate was evaporated to a sirup resulting in a raw material II. I and II were separately purified. I was suspended in acetonitril (100 ml), stirred at 70° C. for 3 h, filtrated of, dried and deprotected according to the following procedure. To the obtained fine powder 25% ammonium hydroxide (300 ml) was added. The stirred reaction mixture was kept closed at ambient temperature for 3 days and has been concentrated afterwards. The resulting sirup formed by adding CH$_3$OH and vigorously stirring a fine precipitate, which was filtered and dried. The obtained residue was dissolved in a small volume of water and purified by flash chromatography on a self-packed RP-18 reversed phase column (LiChroprep, 40-60 μm) using distilled water as eluent. The desired compounds of the fractioned eluat were identified by UV absorption (254 nm). The combined fractions of the first eluted UV-absorbing main peak were evaporated to a sirup forming a fine precipitate by adding MeOH and vigorous stirring. The filtered precipitate was dried resulting in the first part of 6a. The purification of II was performed according to the following procedure. By adding H$_2$O to II a precipitate was built and removed by filtration. The evaporated filtrate was dissolved in a small volume of H$_2$O and chromatographically purified on a RP-18 column as described for I. Afterwards it was deprotected using 25% ammonium hydroxide according to the described procedure resulting in the second part of 6a. The isolated products I and II were combined resulting 15.6 g 6a in a yield of 55%. MS (FAB$^-$) 476.0, [M-H$^-$], 498.0 [M+Na$^-$], 520.1 [M+2Na$^-$]. Anal. calcd. C$_{13}$H$_{20}$FN$_3$Na$_2$O$_{11}$P$_2$*2.5H$_2$O (566.29); C, 27.57, H, 4.45, N, 7.42. Found: C, 27.31, H, 4.33, N, 7.57), $^1$H-NMR (400 MHz, D$_2$O): δ=1.87-2.05 (m, 4H, 2x-CH$_2$—, H2", H3"), 2.19-2.44 (m, 2H, H2') 3.43 (m, 2H, H1") 3.74 (dd, 1H, J1=5.0 Hz, J2=12.5 Hz, H5'α), 3.82 (dd, 1H, J1 3.6 Hz, J2=12.5 Hz, H5'β), 3.99-4.04 (m, 1H, H3'), 4.39-4.44 (m, 1H, H4'), 6.21 (m, 1H, H1'), 7.83 (d, 1H, J$_{HF}$=6.7 Hz, H6); $^{13}$C-NMR (100 MHz, D$_2$O: δ=23.2 (C3"), 31.2 (C2"), 39.2 (C2'), 41.1 (C1"), 61.2 (C5'), 70.4 (C3'), 73.9 (t, J$_{CP}$=131 Hz, P—C—P), 85.9 (C1'), 86.6 (C4'), 123.4 (d, J$_{CF}$=33.4 Hz, C6), 138.1 (d, J$_{CF}$=243.4 Hz, C5), 155.8 (C2), 160.0 (C4); $^{31}$P-NMR (161 MHz, D$_2$O) δ=18.4 ppm.

2.2 Synthesis of N$^4$-[butyl-(4-hydroxy-4-phosphono)phosphonate]-1-(β-D-arabinofuranosylcytosine (araU-alendronate) (6b)

This duplex drug was obtained by linking 3b (21 g, 50 mmol) and 4 (16.2 g, 50 mmol) in the similar manner as described above. Yield 11.7 g (42%) of 6b; MS (FAB$^-$) 474.1 [M-H$^-$], 496.1 [M+Na$^-$], 518.2 [M+2Na$^-$]. Anal. calcd. C$_{13}$H$_{21}$N$_3$Na$_2$O$_{12}$P$_2$*2H$_2$O (555.29) C, 28.12; H, 5.54; N, 7.57. Found C, 28.18; H, 4.75; N, 7.90. $^1$H-NMR (400 MHz, D$_2$O): δ=1.84-2.09 (m, 4H, H2", H3"), 3.30-3.41 (m, 2H, H1"), 3.78-3.94 (m, 2H, H5'), 3.95-4.04 (m, 1H, H4'), 4.06-4.16 (m, 1H, H3'), 4.37-4.43 (m, 1H, H2'), 4.8 (s, br, OH+NH+D$_2$O), 5.93-6.0 (m, 1H, H1'), 6.15-6.22 (m, 1H, H5), 7.62-7.69 (m, 1H, H6). $^{13}$C-NMR (100 MHz, D$_2$O: δ=23.1 (C1"), 31.0 (C2"), 41.3 (C3"), 60.7 (C5'), 75.4 (C2'), 75.5 (C3'), 82.9 (C4'), 85.8 (C1'), 96.4 (C5), 140.6 (C6), 157.3 (C2), 163.6 (C4). $^{31}$P-NMR (161 MHz, D$_2$O) δ=18.1 ppm.

2.3 Synthesis of N$^4$-[butyl-(4-hydroxy-4-phosphono)phosphonate]-5-methyl-3'-azido-2',3'-dideoxycytidine (AZT-alendronate) (6c)

This duplex drug was obtained by linking 3c (3.6 g, 10 mmol) and 4 (3.24 g 10 mmol) in the similar manner as described above. Yield 2.0 g (35%) of 6c; MS (FAB$^-$) 497.0 [M-H$^-$]; 519.1 [M+Na$^-$]; 541.1 [M+2Na$^-$]. Anal. calcd. C$_{14}$H$_{22}$N$_6$Na$_2$O$_{10}$P$_2$*3H$_2$O (596.35), C, 28.20; H, 4.73; N, 14.09. Found: C, 27.92; H, 4.55; N, 14.45. $^1$H-NMR (400 MHz, D$_2$O): δ=1.86-2.05 (m, 7H, H7, H2", H3"), 2.35-2.52 (m, 2H, H1"), 3.38-3.52 (m, 2H, H2'), 3.78 (dd, 1H, J1=4.7 Hz, J2=12.5 Hz, H5'a), 3.86 (dd, 1H, J1=3.6 Hz, J2=12.5 Hz, H5'b), 4.0 (m, 1H, H3'), 4.31 (dt, 1H, J1=5.4 Hz, J2=7.2 Hz, H4'), 4.8 (s, br, D$_2$O+NH+OH), 6.18 (dd, 1H, J1=J2=6.4 Hz, H1'), 7.49 (s, 1H, H6). $^{13}$C-NMR (100 MHz, D$_2$O): δ=12.4 (CH$_3$), 22.4 (C3"), 31.2 (C2"), 36.5 (C1"), 41.6 (C2'), 60.0 (C5'), 61.0 (C3'), 73.9 (t, J$_{CP}$=131 Hz, P—C—P), 83.9 (C1'), 85.4 (C4'), 105.5 (C5), 136.4 (C6), 157.5 (C2), 163.5 (C4). $^{31}$P-NMR (161 MHz, D$_2$O) δ=18.5 ppm.

2.4 Synthesis of N$^4$-[propyl-(3-hydroxy-3-phosphono)phosphonate]-5-fluoro-2'-deoxycytidine (5-FdU-pamidronate) (7a)

This duplex drug was synthesised by coupling 3a (9.5 g, 25 mmol) and 5 (6.9 g, 25 mmol) in analogy to the synthesis route of 6a resulting in 7a. Yield 6.5 g (48%).
MS (FAB$^-$) 462.0 [M-H$^-$]; 484.0 [M+Na$^-$]; 505.9 [M+2Na$^-$]. Anal. calcd. C$_{12}$H$_{18}$FN$_3$Na$_2$O$_{11}$P$_2$*2H$_2$O (543.26) C, 26.53; H, 4.08; N, 7.73. Found C, 26.28; H, 4.26; N, 8.22 $^1$H-NMR (400 MHz, D$_2$O): δ=2.19-2.45 (m, 4H, H2'+H2"), 3.68-3.87 (m, 4H, H5'+H1"), 3.99-4.05 (m, 1H, H3'), 4.39-4.50 (m, 1H, H4'), 6.18-6.25 (m, 1H, H1'), 7.83 (d, 1H, J$_{HF}$=6.0 Hz, H6). $^{13}$C-NMR (100 MHz, D$_2$O): δ=32.3 (C2"), 36.6 (C1"), 39.2 (C2'), 61.2 (C5'), 70.4 (C3'), 72.9 (t, J$_{CP}$=132.7 Hz, P—C—P), 85.9 (C1'), 86.6 (C4'), 123.4 (d, J$_{CF}$=33.4 Hz, C6), 138.1 (d, J$_{CF}$=243 Hz, C5), 155.6 (d, J$_{CF}$=13.9 Hz, C4), 155.9 (C2). $^{31}$P-NMR (161 MHz, D$_2$O) δ=17.8 ppm.

2.5 Synthesis of $N^4$-[propyl-(3-hydroxy-3-phosphono)phosphonate]-1-β-D-arabinofuranosylcytosine (araU-pamidronate) (7b)

The substitution of 3a (42 g, 0.1 mol) with 5 (27.4 g, 0.1 mol) in analogy to the preparation of 6a resulted in the duplex drug 7b. Yield 25.3 g, (45%). MS (FAB$^-$) 460.1 [M-H$^-$]; 482.2 [M+Na$^-$]. Anal. calcd $C_{12}H_{20}N_3NaO_{12}P_2*2H_2O1.5NH_3$ (562.86) C, 26.46; H, 5.27; N, 11.57. Found: C, 26.95; H, 5.56; N, 11.80. $^1$H-NMR (400 MHz, D$_2$O): δ=1.93-1.98 (m, 2H, H2''), 2.76-2.81 (m, 2H, H1''), 3.75-3.92 (m, 2H, H5'), 3.92-4.01 (m, 1H, H4'), 4.04-4.39 (m, 1H, H3'), 4.34-4.39 (m, 1H, H2'), 5.86-5.92 (m, 1H, H1'), 6.12-6.18 (m, 1H, H5), 7.64-7.75 (m, 1H, H6); $^{13}$C-NMR (100 MHz, D$_2$O): δ=32.4 (C1''), 38.4 (C2''), 60.8 (C5'), 75.4 (C2'), 75.5 (C3'), 83.6 (C4'), 85.6 (C1'), 96.5 (C5), 140.7 (C6), 157.2 (C2), 163.2 (C4). $^{31}$P-NMR (161 MHz, D$_2$O) δ=17.8 ppm.

2.6 Synthesis of $N^4$-[propyl-(3-hydroxy-3-phosphono)phosphonate]-5-methyl-3'-azido-2',3'-dideoxycytidine (AZT-pamidronate) (7c)

By substitution of 3c (1.8 g, 5 mmol) with 5 (1.4 g, 5 mmol) in analogy to the preparation of 6a the duplex drug 7c was obtained. Yield 1.2 g (41%). MS (FAB$^-$) 483.0 [M-H$^-$]; 505.1 [M+Na$^-$], 527.1 [M+2Na$^-$]. Anal. calcd. $C_{13}H_{20}N_6Na_2O_{10}P_2*3.5H_2O$ (591.34). C, 26.41; H, 4.60; N, 14.21. Found: C, 25.98, H, 4.46; N, 14.75. $^1$H-NMR (400 MHz, D$_2$O): δ=1.93 (s, 3H, CH$_3$), 2.17-2.31 (m, 2H, H2''), 2.35-2.52 (m, 2H, H1''), 3.69-3.89 (m, 4H, H2'+H5'), 3.97-4.03 (m, 1H, H3'), 4.28-4.35 (m, 1H, H4'), 4.8 (s, br, OH+NH+D2O), 6.16-6.22 (m, 1H, H1'), 7.49 (s, 1H, H6). $^{13}$C-NMR (100 MHz, D$_2$O): δ=12.3 (C7), 32.6 (C2''), 36.4 (C1''), 37.2 (C2'), 59.9 (C5'), 61.0 (C3'), 73.2 (t, $J_{CP}$=130 Hz), 83.9 (C1'), 85.3 (C4'), 105.6 (C5), 136.3 (C6), 157.5 (C2), 163.1 (C4). $^{31}$P-NMR (161 MHz, D$_2$O) δ=18.0 ppm.

C. Test Example

Example 3

In Vitro Growth Inhibition of Different Tumor Cell Lines by 5-FdU-alendronate (6a)

The in-vitro cytostatic action of the compounds according to the invention on different tumor cell lines can be demonstrated with the following test setup.

On day 0, a series of microtiter plates is inoculated with the tumor cells and preincubated for 24 h. Then the compound according to the invention is added to the cells. After incubation for 48 hours, the cells are fixed in situ, washed and dried. Then sulfor-hodamine B (SRB), a pink dye that binds to the fixed cells, is added and the cells are washed again. The dye that remains represents the adherent cell mass and is determined spectroscopically. The automatically acquired data are evaluated by computer.

Testing of 60 tumor cell lines with 10 μM 5FdU-alendronate (compound 6) and a short 48 h incubation for example showed variable growth inhibition between 5% and 32% of 11 tumor cell lines. The test results are summarized in the following Table 1

TABLE 1

In vitro growth inhibition of tumor cell lines under treatment with 5-FdU-alendronate. The cytostatic effects of 5-FdU-alendronate is expressed by growth percent under treatment with 10 μM dose of the duplex drug.

| Panel/Cell line | Growth [%][1] 5-FdU-alendronate 6a (10 μM)[2] |
|---|---|
| Leukemia | |
| HL-60 (TB) | 61.75 |
| Non-small cell lung cancer | |
| EKVX | 82.45 |
| HOP-62 | 93.16 |
| NCI-H322M | 88.84 |
| CNS cancer | |
| SF-268 | 86.64 |
| SF-539 | 94.79 |
| SNB-75 | 87.12 |
| Melanomas | |
| MALME-3M | 89.24 |
| MDA-MB-435 | 86.95 |
| Ovarian cancers | |
| OVCAR-3 | 88.34 |
| Renal cancers | |
| CAKI-1 | 79.14 |

[1]100% refers to the growth observed for the corresponding cell line in the absence of the drug
[2]for alendronate alone (10 μM) no growth inhibiting effect was observed

Example 4

Hydroxyapatite Binding of Nucleoside-BPs

It is known that the BPs moiety of conjugates preserves its high affinity for the bone matrix even when coupled to a bulk residue[17,41] The high affinity to the bone matrix is based on the strong binding properties of BPs to hydroxyapatite[42, 43, 44]. For this reasons, we analyzed the adsorption properties of 5-FdU-ale and 5-FdU to hydroxyapatite.
a) 5-FdU and Untreated 5-FdU-Alendronate (5-FdU-ale)

5-FdU (246 mg, 1 mmol) or 5-FdU-ale (475 mg) were dissolved in distilled water (100 ml). The $A_{260}$-units of the obtained solution and the absorbance ratios of 250/260 and 280/260 were determined using an UV-spectrophotometer. After addition of solid hydroxyapatite as listed in Table 2 the obtained suspension was stirred at room temperature for 24 h. Then, an aliquot (1 ml) of the suspension was filtered through a sterile filter and the $A_{260}$-units of the filtrate were measured. The amount of drug bound to hydroxyapatite was calculated on the basis of the decreased $A_{260}$-units of the suspension.
b) Acidified Pretreatment 5-FdU-Alendronate A solution of 5-FdU-ale (475 mg) in 100 ml H$_2$O was acidified to pH 2 by adding HCl and stirred at 50° C. for 24 h, followed by neutralization with solid sodium carbonate. UV-active degradation products were not detectable at 254 nm by TLC-analysis with CHCl$_3$/MeOH (80:20) using silica gel plates. The hydroxyapatite binding of the pretreated 5-FdU-ale was analyzed as described above.

As summarized in Table 2, only 15% of 5-FdU were adsorbed to hydroxyapatite, whereas 5-FdU-ale adsorption was approximately sixfold higher (87%). The binding study was also used for an indirect assessment of the stability of the nucleoside-BPs in acidic conditions. Binding was reduced by 13% compared to the untreated compound when a solution of 5-FdU-ale was acidified to pH 2 and kept at 50° C. during 24 h prior to the adsorption to hydroxyapatite. The unchanged A250/260 and 280/260 UV-ratio indicate that no cleavage of 5-FdU-ale into the monomer 5-FdU+ ale occurs during treatment with hydroxyapatite under the used conditions.

A TLC analysis of the supernatant did not reveal any UV-active compounds like 5-fluorouracil or 5-FdU. Thus, the absence of UV-active compounds allows to conclude that 5-FdU-ale is very stable in acidic conditions.

TABLE 2

Binding of 5-FdU and 5-FdU-alendronate (5-FdU-ale) to hydroxyapatite

| Drug | Drug (mg) | Hydroxy-apatite (g) | UV-adsorption | | | Bound drug | |
|---|---|---|---|---|---|---|---|
| | | | $A_{260}$-units | Ratio 250/260 | 280/260 | mg | % |
| 5-FdU | 246 | 0 | 8050 | 0.61 | 1.01 | 0 | 0 |
| 5-FdU | 246 | 7 | 6860 | 0.63 | 1.10 | 37 | 15 |
| 5-FdU-ale | 475 | 0 | 7590 | 1.00 | 1.27 | 0 | 0 |
| 5-FdU-ale | 475 | 5 | 4500 | 1.02 | 1.23 | 195 | 41 |
| 5-FdU-ale | 475 | 7 | 990 | 1.04 | 1.17 | 414 | 87 |
| 5-FdU-ale* | 475 | 7 | 1950 | 1.00 | 1.23 | 352 | 74 |

The $A_{260}$-units of aqueous solutions/suspensions (100 ml) containing 5-FdU or 5-FdU-ale were measured before and after the addition of solid hydroxyapatite. Amounts of drug bound were calculated on the basis of the decreased $A_{260}$-units of the supernatant.
*Acid pretreatment

REFERENCES AND NOTES

1. Fleisch, H. *Drugs* 1991, 42, 919.
2. Vepsäläinen, J. J. *Curr Med Chem* 2002, 9, 1201.
3. Widler, L.; Jaeggi, K. A.; Glatt, M.; Muller, K.; Bachmann, R.; Bisping, M.; Born, A. R.; Cortesi, R.; Guiglia, G.; Jeker, H.; Klein, R.; Ramseier, U.; Schmid, J.; Schreiber, G.; Seltenmeyer, Y.; Green, J. R. *J Med Chem* 2002, 45, 3721.
4. Brown, J. E.; Cook, R. J.; Major, P.; Lipton, A.; Saad, F.; Smith, M.; Lee, K. A.; Zheng, M.; Hei, Y. J.; Coleman, R. E. *J Natl Cancer Inst* 2005, 97, 59.
5. Coleman, R. E. *Br J Cancer* 2008, 98, 1736.
6. Ghosh, S.; Chan, J. M.; Lea, C. R.; Meints, G. A.; Lewis, J. C.; Tovian, Z. S.; Flessner, R. M.; Loftus, T. C.; Bruchhaus, I.; Kendrick, H.; Croft, S. L.; Kemp, R. G.; Kobayashi, S.; Nozaki, T.; Oldfield, E. *J Med Chem* 2004, 47, 175.
7. Sanders, J. M.; Gomez, A. O.; Mao, J.; Meints, G. A.; Van Brussel, E. M.; Burzynska, A.; Kafarski, P.; Gonzalez-Pacanowska, D.; Oldfield, E. *J Med Chem* 2003, 46, 5171.
8. Adzamli, I. K.; Blau, M.; Pfeffer, M. A.; Davis, M. A. *Magn Reson Med* 1993, 29, 505.
9. Adzamli, I. K.; Johnson, D.; Blau, M. *Invest Radiol* 1991, 26, 143.
10. Bhushan, K. R.; Tanaka, E.; Frangioni, J. V. *Angew Chem Int Ed Engl* 2007, 46, 7969.
11. Kubicek, V.; Rudovsky, J.; Kotek, J.; Hermann, P.; Vander Elst, L.; Muller, R. N.; Kolar, Z. I.; Wolterbeek, H. T.; Peters, J. A.; Lukes, I. *J Am Chem Soc* 2005, 127, 16477.
12. Zhang, S.; Gangal, G.; Uludag, H. *Chem Soc Rev* 2007, 36, 507.
13. Vitha, T.; Kubicek, V.; Hermann, P.; Kolar, Z. I.; Wolterbeek, H. T.; Peters, J. A.; Lukes, I. *Langmuir* 2008, 24, 1952.
14. Sturtz, G.; Appéré, G.; Breistol, K.; Fodstad, O.; Schwartsmann, G.; Hendriks, H. R. *Eur. J. Med. Chem.* 1992, 27, 825.
15. Sturtz, G.; Couthon, H.; Fabulet, O.; Mian, M.; Rosini, S. *Eur. J. Med. Chem.* 1993, 28, 899.
16. Fabulet, O.; Sturtz, G. *Phosphorus, Sulfur, and Silicon* 1995, 101, 225.
17. Uludag, H.; Kousinioris, N.; Gao, T.; Kantoci, D. *Biotechnol Prog* 2000, 16, 258.
18. Budman, D. R.; Calabro, A. *Oncology* 2006, 70, 147.
19. Clezardin, P. *Cancer Treat Rev* 2005, 31 Suppl 3, 1.
20. Coleman, R.; Gnant, M. *Curr Opin Support Palliat Care* 2009, 3, 213.
21. Knight, L. A.; Conroy, M.; Fernando, A.; Polak, M.; Kurbacher, C. M.; Cree, I. A. *Anticancer Drugs* 2005, 16, 969.
22. Neville-Webbe, H. L.; Rostami-Hodjegan, A.; Evans, C. A.; Coleman, R. E.; Nolen, I. *Int J Cancer* 2005, 113, 364.
23. Roelofs, A. J.; Thompson, K.; Gordon, S.; Rogers, M. J. *Clin Cancer Res* 2006, 12, 6222s.
24. Santini, D.; Vespasiani Gentilucci, U.; Vincenzi, B.; Picardi, A.; Vasaturo, F.; La Cesa, A.; Onori, N.; Scarpa, S.; Tonini, G. *Ann Oncol* 2003, 14, 1468.
25. Vogt, U.; Bielawski, K. P.; Bosse, U.; Schlotter, C. M. *Oncol Rep* 2004, 12, 1109.
26. Winter, M. C.; Coleman, R. E. *Curr Opin Oncol* 2009, 21, 499.
27. Winter, M. C.; Nolen, I.; Coleman, R. E. *Cancer Treat Rev* 2008, 34, 453.
28. Song, Y.; Chan, J. M.; Tovian, Z.; Secrest, A.; Nagy, E.; Krysiak, K.; Bergan, K.; Parniak, M. A.; Oldfield, E. *Bioorg Med Chem* 2008, 16, 8959.
29. Migianu, E.; Monteil, M.; Even, P.; Lecouvey, M. *Nucleosides Nucleotides Nucleic Acids* 2005, 24, 121.
30. Kalek, M.; Jemielity, J.; Stepinski, J.; Stolarski, R.; Darzynkiewicz, E. *Tetrahedron Letters* 2005, 46, 2417.
31. Divakar, K. J.; Reese, C. B. *J. Chem. Soc., Perkin Trans.* 1 1982, 1171.
32. Gao, Y.; Zhang, P.; Wu, L.; Matsuura, T.; Meng, J. *Synthetic Communications* 2003, 33, 2635.
33. Schott, H.; Häussler, M. P.; Schwendener, R. A. *Liebigs Ann. Chem.* 1994, 465.
34. Schott, H. In *Preparative Scale-Chromatography*; Grushka, E., Ed.: New York Basel; 1989; Vol. 46, 269.
35. Wingen, F.; Sterz, H.; Blum, H.; Moller, H.; Pittermann, W.; Pool, B. L.; Sinn, H. J.; Spring, H.; Schmahl, D. *J Cancer Res Clin Oncol* 1986, 111, 209.
36. Monkkonen, H.; Kuokkanen, J.; Holen, I.; Evans, A.; Lefley, D. V.; Jauhiainen, M.; Auriola, S.; Monkkonen, J. *Anticancer Drugs* 2008, 19, 391.
37. Chen, H.; Wu, L.-Y.; Zeng, J.-C.; Wu, Y. *West China Journal of Pharmaceutical sciences* 2005, 2, 10.
38. Schott, S. *Pharm. Ztg.* 2001, 146, 24.
39. Kieczykowski, G. R.; Jobson, R. B.; Melillo, D. G.; Reinhold, D. F.; Grenda, V. J.; Shinkai, I. *J. Org. Chem.* 1995, 60, 8310.
40. Choi et al., Dental Traumatology, 2010; 26; 476-480.
41. Pan, H.; Sima, M.; Kopeckova P.; Wu, K.; Gao, S.; Liu, J.; Wang, D.; Miller, S. C.; Kopecek, J. *Mol. Pharmacol.* 2008, 5, 548.
42. Papapoulos S. E. *Bone* 2006, 38, 613.
43. Leu, C. T.; Luegmayr, E.; Freedman, L. P.; Rodan, G. A.; Reszka, A. A. *Bone* 2006, 38, 628
44. Nancollas, G. H.; Tang, R.; Phipps, R. J.; Henneman, Z.; Guide, S.; Wu, W.; Mangood, A.; Russell, R. G; Ebetino, F. H. *Bone* 2006, 38, 617.

The content of the documents cited herein is incorporated by reference

The invention claimed is:

1. A bisphosphonate of the general formula I

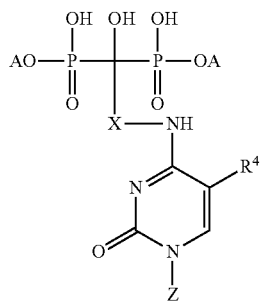

(I)

wherein
residues A independently of each other represent a proton or a monovalent metal cation;
X represents a straight-chain or branched alkylene bridge;
Z represents H or a 5- or 6-membered carbo- or heterocyclic, optionally mono- or poly-substituted ring, and
$R^4$ represents hydrogen, halogen, amino, hydroxy, trifluoromethyl, linear or branched alkyl, linear or branched alkoxy or bromovinyl.

2. The compound of claim 1 of the general formula Ia

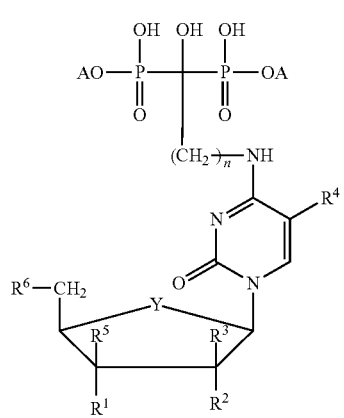

(Ia)

wherein
residues A independently of each other represent a proton, or a monovalent metal cation;
Y represents O or S;
n represents an integer of 1, 2, 3 or 4;
$R^1$, $R^2$, $R^3$ and $R^5$ independently of each other represent hydrogen, halogen, fluoromethylene, hydroxy, azido, cyano, linear or branched alkoxyl, acyl, lower alkinyl;
$R^4$ represents hydrogen, halogen, amino, hydroxy, trifluoromethyl, linear or branched alkyl, linear or branched alkoxyl or bromovinyl;
$R^6$ represents hydrogen, halogen, amino, hydroxy, phosphate, linear or branched alkyl, linear or branched alkoxyl or acyl.

3. The compound of claim 2, wherein
residues A independently of each other represent a proton, or a alkali metal cation;
Y represents O;
n represents an integer of 2 or 3;
$R^1$ represents hydrogen, halogen, azido or hydroxy;
$R^2$ represents hydrogen or hydroxy;
$R^3$ represents hydrogen or hydroxy;
$R^4$ represents hydrogen, halogen, or linear or branched alkyl;
$R^5$ represents hydrogen or lower alkinyl; and
$R^6$ represents hydroxy or acyl.

4. The compound of claim 2, wherein
residues A independently of each other represent $Na^+$ or $K^+$;
Y represents O;
n represents an integer of 2 or 3;
$R^1$ represents azido or hydroxy;
$R^2$ represents hydrogen or hydroxy;
$R^3$ represents hydrogen or hydroxy;
$R^4$ represents hydrogen, fluoro or methyl;
$R^5$ represents hydrogen; and
$R^6$ represents hydroxy.

5. A method for the treatment of tumours or viral infections in a mammal, comprising administering the compound of claim 1 to the mammal.

6. A method for the treatment of bone tumours in a mammal, comprising administering the compound of claim 1 to the mammal.

7. A pharmaceutical composition comprising in a pharmaceutically acceptable carrier at least one compound of claim 1.

8. A method of preparing a compound of general formula I as defined in claim 1, which method comprises
a) reacting a compound of general formula II

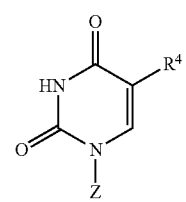

(II)

wherein Z and $R^4$ are as defined above, provided that if anyone of residues Z and $R^4$ contains a hydroxy group said hydroxy group is a protected hydroxy group,
with triazole to for a compound of formula III

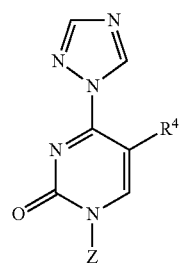

(III)

b) reacting a compound of formula III with an aminophosphonate of the general formula IV

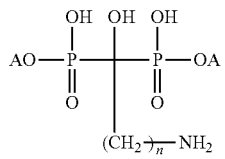

(IV)

c) and isolating the desired product optionally after removing any protecting groups.

9. A method of preparing a compound of general formula Ia as defined in claim 2, which method comprises a) reacting a compound of general formula IIa

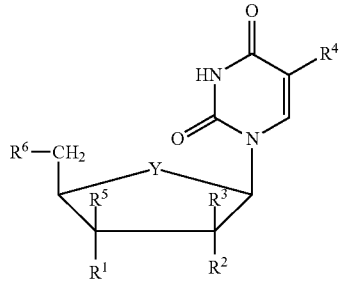

(IIa)

wherein Y and $R^1$, $R^2$, $R^3$, $R^4$, $R^5$ and $R^6$ are as defined above, provided that if anyone of residues $R^1$ to $R^6$ shall be hydroxy group said group is a protected hydroxy group, with triazole to for a compound of formula IIIa

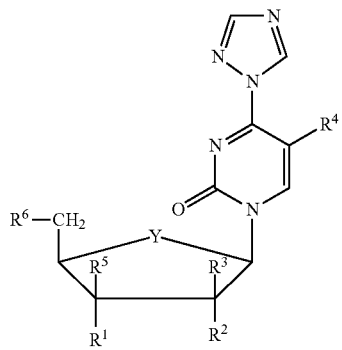

(IIIa)

b) reacting a compound of formula IIIa with an aminophosphonate of the general formula IV

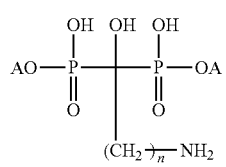

(IV)

c) and isolating the desired product optionally after removing any protecting groups.

10. The method of claim 9, wherein the aminophosphonate compound is selected from alendronate and pamidronate.

11. The method of claim 6, wherein the bone tumours are metastatic bone tumours.

12. The method of claim 5, wherein the mammal is a human.

13. The method of claim 6, wherein the mammal is a human.

14. The composition of claim 7, wherein the composition further comprises at least one further therapeutically active ingredient.

\* \* \* \* \*